(12) United States Patent
Gray

(10) Patent No.: US 9,302,973 B2
(45) Date of Patent: Apr. 5, 2016

(54) APPARATUS AND PROCESS FOR PURIFICATION OF AROMATIC CARBOXYLIC ACID

(71) Applicant: Johnson Matthey Davy Technologies Limited, London (GB)

(72) Inventor: Julian Stuart Gray, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

(21) Appl. No.: 14/433,831

(22) PCT Filed: Oct. 31, 2013

(86) PCT No.: PCT/GB2013/052844
§ 371 (c)(1),
(2) Date: Apr. 6, 2015

(87) PCT Pub. No.: WO2014/072686
PCT Pub. Date: May 15, 2014

(65) Prior Publication Data
US 2015/0274631 A1 Oct. 1, 2015

(30) Foreign Application Priority Data
Nov. 6, 2012 (GB) .................................. 1219983.2

(51) Int. Cl.
*C07C 51/42* (2006.01)
*B01J 8/02* (2006.01)
*B01J 8/04* (2006.01)
*C07C 51/487* (2006.01)

(52) U.S. Cl.
CPC ................. *C07C 51/42* (2013.01); *B01J 8/025* (2013.01); *B01J 8/0242* (2013.01); *B01J 8/0278* (2013.01); *B01J 8/0446* (2013.01); *B01J 8/0453* (2013.01); *C07C 51/487* (2013.01); *B01J 2208/00849* (2013.01); *B01J 2208/00893* (2013.01); *B01J 2208/00911* (2013.01); *B01J 2208/024* (2013.01)

(58) Field of Classification Search
CPC ...... C07C 51/41; C07C 51/487; B01J 8/0242; B01J 8/0446; B01J 8/0278; B01J 8/0453; B01J 8/025; B01J 2208/00893; B01J 2208/024; B01J 2208/00911; B01J 2208/00849
IPC ........................................... C07C 51/487, 63/26
See application file for complete search history.

(56) References Cited

U.S. PATENT DOCUMENTS

| | | |
|---|---|---|
| 5,138,106 A | 8/1992 | Wilmott et al. |
| 5,157,168 A | 10/1992 | Wilmott et al. |
| 5,420,344 A | 5/1995 | Izumisawa et al. |
| 5,536,856 A | 7/1996 | Harrison et al. |
| 5,672,781 A | 9/1997 | Koehler et al. |
| 6,187,974 B1 | 2/2001 | Wieczorek et al. |
| 2011/0054225 A1 | 3/2011 | Boensch et al. |

FOREIGN PATENT DOCUMENTS

| | | |
|---|---|---|
| WO | 9410112 | 5/1994 |
| WO | 2004060848 A1 | 7/2004 |
| WO | 2007045457 A1 | 4/2007 |
| WO | 2010096626 A1 | 8/2010 |
| WO | 2011100682 A2 | 8/2011 |
| WO | 2013072664 A1 | 5/2013 |

OTHER PUBLICATIONS

International Search Report and Written Opinion for PCT/GB2013/052844, dated Jan. 29, 2014.

*Primary Examiner* — Shailendra Kumar
(74) *Attorney, Agent, or Firm* — Armstrong Teasdale LLP

(57) ABSTRACT

In a reaction vessel for the purification of crude aromatic carboxylic acid, a bed of hydrogenation catalyst having a vapor space is located above the hydrogenation catalyst bed. A packed bed and a holdup section are located within the vapor space and spaced above the catalyst bed. The reaction vessel has means for introducing crude aromatic carboxylic acid and means for introducing hydrogen to the reaction vessel at respective locations such that in use the crude carboxylic acid contacts the hydrogen in the packed bed. The reaction vessel also has means for removing purified aromatic carboxylic acid.

15 Claims, 1 Drawing Sheet

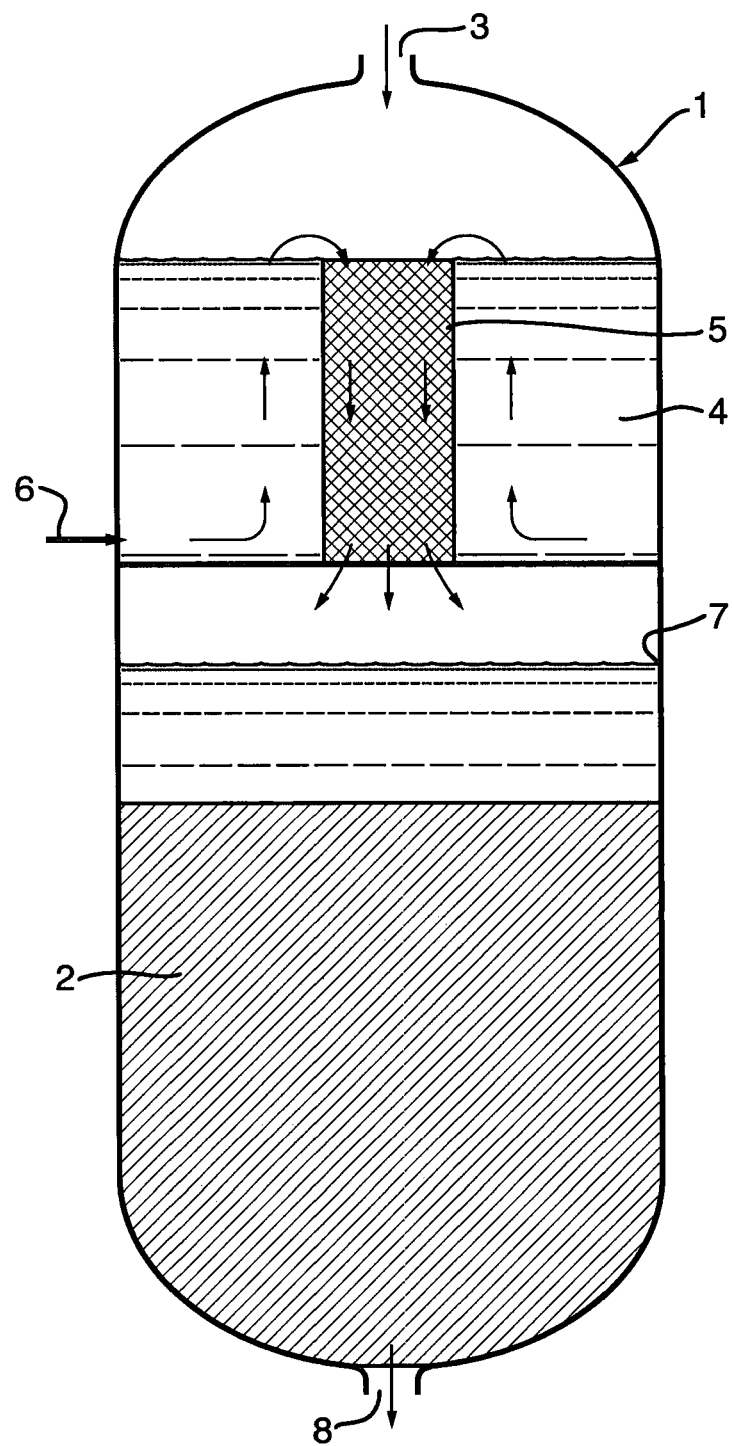

APPARATUS AND PROCESS FOR PURIFICATION OF AROMATIC CARBOXYLIC ACID

This application is a 371 of PCT/GB2013/052844, filed on Oct. 31, 2013.

The present invention relates to a reaction vessel and a process for the purification of crude aromatic carboxylic acids. More specifically, the invention relates to a reaction vessel and a process for the purification of aromatic polycarboxylic acids, and in particular of terephthalic acid or isophthalic acid.

Typically crude terephthalic acid is produced by the oxidation of p-xylene. The oxidation is conducted using acetic acid as solvent in the presence of a catalyst. The solution is then cooled in a stepwise manner to crystallise the terephthalic acid. The crude terephthalic acid is then removed from the acetic acid solvent and this is generally done by filtration. So-called "crude" terephthalic acid is most economically produced with a purity of about 99.6-99.7 wt % with the major impurity generally being 4-carboxybenzaldehyde which is the intermediate in the reaction chain immediately prior to the production of the terephthalic acid. Since 4-carboxybenzaldehyde and other impurities in the crude terephthalic acid such as p-toluic acid and benzoic acid have a single carboxylic acid end group and so act as chain stoppers in downstream polymerisation reactions in which the terephthalic acid is reacted with ethylene glycol to form the polyester product their presence is undesirable. Thus whilst the level of purity of crude terephthalic acid is sufficient for some purposes, further purification of this crude product is generally required such as where the terephthalic acid is to be used in the production of polyesters. Purified terephthalic acid has a significantly lower content of impurities with the total content of p-toluic acid and 4-carboxybenzaldehyde desirably being less than 200 ppm w/w. This ensures that the purified terephthalic acid is of sufficient purity to make the polymeric products which can be used to manufacture bottles, films, polyester fibres and filaments.

Other aromatic carboxylic acids are produced by oxidation of an aromatic compound in a solvent in the presence of a catalyst. The product of the oxidation reaction will not generally be sufficiently pure for the uses to which they are to be put and a purification step will be required.

In the purification of, for example, terephthalic acid, the crude terephthalic acid, which is contaminated with undesired impurities is dissolved in water to produce a clear solution. The solution is then passed through a heterogeneous hydrogenation catalyst where the impurities are hydrogenated to a form that makes them more easily separated from the desired terephthalic acid. Thus, the hydrogenation step enables high purity terephthalic acid to be produced. By "high" purity we mean that as a minimum the purified terephthalic acid has a higher purity compared to the crude terephthalic acid and preferably have a p-toluic acid and 4-carboxybenzaldehyde content of 200 ppm w/w or less.

One example of a process in which the impurities are hydrogenated is described in U.S. Pat. No. 3,584,039 in which an aqueous solution of crude terephthalic acid is hydrogenated in the presence of a catalyst. The treated solution is separated from the catalyst and the pure terephthalic acid is then recovered by crystallisation. The crystals can then be separated from the impurities which are retained in the mother liquor. In U.S. Pat. No. 3,584,039 the catalyst is a Group VIII Noble metal catalyst on an inert support. Typically commercially the catalyst is 0.5% w/w palladium on a carbon base support.

As the catalyst is quite fragile, in order to maximise the life of the catalyst bed, the hydrogenation reactor is generally operated with a fully flooded catalyst bed. In this case there is only liquid flowing over the catalyst bed and a liquid level is maintained above the catalyst bed. It follows that the hydrogen required for the hydrogenation reaction must be dissolved in the liquid feed to the hydrogenation reactor before the solution reaches the liquid level and flows down through the hydrogenation catalyst bed. Operating with a fully flooded bed means that if insufficient hydrogen is dissolved in the liquid before it reaches the catalyst bed, then not all of the impurities can be hydrogenated such that the desired level of purity will not be achieved.

Historically, in the simplest form, the dissolution of hydrogen into the liquid feed stream to the hydrogenation reactor has been achieved by flowing the dissolved crude product stream into the reaction vessel via a basic ring type distributor. The distributor enables the crude liquid feed to flow downwardly in liquid columns through a vapour space located above the liquid level of the hydrogenation catalyst bed. The vapour space comprises water vapour and hydrogen. The hydrogen is generally added directly into the vapour space at a rate which is equivalent to the rate at which hydrogen is being dissolved into the liquid solution of crude acid in water in order to maintain the pressure in the vessel.

The rate at which the hydrogen dissolves into the liquid stream is dependent on the partial pressure of hydrogen in the vapour space as well as the liquid surface area. There are limits on the partial pressure of hydrogen that can be achieved. The partial pressure is primarily limited by the mechanical design pressure of the reactor vessel as well as the maximum delivery pressure available from the pumps upstream that are feeding the liquid stream into the reactor.

The main problem with this ring type distributor system is that over time it has been found that the edges of the holes erode and become enlarged. Eventually the metal between adjacent holes is eroded sufficiently for the holes to combine into an elongated opening. This erosion of the holes within the distributor gradually reduces the effectiveness of this method. This is because as the number of liquid columns passing through the vapour space decreases, the surface area of liquid available to contact the hydrogen is also reduced. Thus, lower hydrogen concentrations are achieved in the liquid due to the reduction in mass transfer area.

Ultimately this adversely affects the plant operation. This means that either the reactor rate has to be reduced or the incoming feed quality has to be improved to reduce the levels of impurities in the feed and hence reduce the hydrogenation load. These effects impact on the economic viability of producing the desired purified product.

Eventually the erosion of the ring distributor will require the plant to be stopped so that the distributor can be replaced.

Even when the plant is operating with a new liquid ring distributor, the amount of liquid surface area available may not necessarily be enough to fully saturate the liquid solution with hydrogen.

It has therefore been desirable to consider alternative designs in order to further increase the liquid surface area in the vapour space of the reactor.

A further problem associated with this type of ring type distributor is that additional height has to be provided in the reactor to provide sufficient area for the contact between the liquid and the hydrogen. This additional height is associated with providing sufficiently tall columns of liquid to achieve the required liquid surface area.

One alternative arrangement is described in WO2011/100682. In this arrangement a liquid distributor is used which comprises a perforated circular disc or perforated circular open pipe or channel with a diameter of about 0.3 to 0.9 of the purification reactor vessel diameter. The perforated disc breaks the incoming liquid into a plurality of small liquid columns which increases the liquid surface area over that achieved with conventional ring type distributors.

Whilst this arrangement offers improvements in the amount of available surface area, it does suffer from various disadvantages and drawbacks. In particular, the height of the reaction vessel has to be increased further over conventional arrangements to allow for installation of the distributor and additional height has to be provided to generate the liquid surface area below the distributor.

A further problem is that the distributor plate has to be installed such that it is level to ensure that a uniform flow of liquid from the plate is achieved. This is important since any imbalance in liquid flow across the perforated distributor plate can cause a reduction in the liquid surface area. This requirement makes installation of the plate difficult.

An alternative arrangement for allowing a liquid feed to have hydrogen saturated therein is described CN202179958. In this arrangement, a packed section is located above the main catalyst bed. The packed section extends across the whole cross section of the reactor.

An alternative arrangement is disclosed in US2002127160. In this arrangement, a sub-assembly is described to provide contact between a liquid phase and a gas phase which are in downflow mode. The sub-assembly comprises at least one distributor tray located above a bed of granular solid, comprising a plurality of downcomers each surmounted by at least one jet distributer device and each having in its upper portion at least one cross section of flow for entry of the major portion of the gas phase into the downcomer and, between the upper portion and the lower portion of the downcomer above the tray, and at least one cross section of flow for entry of the major portion of the liquid phase into the downcomer, and in its lower portion at least one cross section of flow of the mixture formed in the downcomer for distributing it over the bed of granular solid located below the lower portion, each downcomer containing at least one packing extending across the whole of the transverse cross-section of the downcomer between its upper portion and its lower portion in the circulation zone, constituted by cells through which said liquid and said gas phase pass, said cells orientating the circulation of fluids inside said downcomer in a substantially radial direction. However, this arrangement is complex to construct and requires substantial height in the reaction vessel above the catalyst bed.

It is therefore desirable to provide an alternative process which enables the feed to the hydrogenation catalyst bed to be fully saturated with hydrogen. It is also preferred that this is achieved whilst minimising the height of the vessel in which the hydrogenation reaction is performed.

This is achieved by providing a packed section and a liquid holdup section in the vapour space of the reaction vessel.

Thus according to a first aspect of the present invention there is provided a reaction vessel for the purification of crude aromatic carboxylic acid comprising:
- a bed of hydrogenation catalyst having a vapour space located above said hydrogenation catalyst bed;
- a packed bed and a holdup section located within the vapour space and spaced above said catalyst bed;
- means for introducing crude aromatic carboxylic acid and means for introducing hydrogen to the reaction vessel at respective locations such that in use the crude carboxylic acid contact the hydrogen in the packed bed; and
- means for removing purified aromatic carboxylic acid.

By this means the crude aromatic carboxylic acid may be fully saturated with hydrogen. The crude aromatic carboxylic acid is generally provided as an aqueous solution. The "crude" carboxylic acid feed may be the direct product from the process for the production of the carboxylic acid feed or it may be a feed which has already been subject to some purification process.

The packed bed will generally be provided with sufficient voidage that the liquid contacts the hydrogen in the vapour space. The packed bed will not be flooded. With this arrangement saturation can be achieved without the additional height requirement of prior art arrangements. In one arrangement the reduction in height will be of the order of 1 to 1.5 m in a vessel of typically 9 to 10 m height. Without wishing to be bound by any theory, the resulting vessel height reduction is achieved since the required mass transfer is not dependent on the height of falling liquid streams.

Typically the means for introducing the hydrogen will be located at or near the top of the vessel. In this arrangement, the hydrogen and the crude carboxylic acid flow co-currently through the packed bed. Additionally it may be added at any other suitable point including at or near the bottom of the vessel and/or between the packed bed and the catalyst bed. In one arrangement, it may be added into the liquid holdup section.

However, in some arrangements the introducing means may be configured to introduce the hydrogen below the packed bed such that the introduced hydrogen flows upwards counter-currently to the liquid flowing downwardly through the packed bed.

The crude aromatic carboxylic acid will generally be supplied in a suitable solution or as a slurry therein. Any suitable solvent may be used. For the purposes of the present application the reference to the "carboxylic acid" should be understood to be the acid and its solvent. The use of a holdup section generally provides sufficient residence time to ensure that all of the crude aromatic carboxylic acid solids are fully dissolved in the solvent before it is contacted with the hydrogen in the packed bed. In this arrangement, the liquid is generally added into the liquid holdup section.

Any configuration may be used for the liquid holdup section and the packed bed which achieve the required result. In one arrangement, the liquid holdup section may be located at any position above the packed bed. In this arrangement, any suitable means may be used to remove the liquid from the liquid holdup section and supply it to the packed bed. In this arrangement, the packed bed may extend across the reactor.

In a preferred arrangement, the liquid holdup section will be located as an annulus around a central downcomer. In this arrangement the inlet means for the aromatic carboxylic acid will generally be located at or near the bottom of the liquid holdup section. In this arrangement, the packed bed may be located below the downcomer or may be located within the downcomer.

In one arrangement, a pluralities of downcomers may extend through the liquid holdup section.

In a still further alternative arrangement the holdup section may be located centrally with the packed bed being located as an annulus around it.

Any suitable packing may be used provided that it provides a plurality of surfaces which will be wetted by the crude aromatic carboxylic acid solution to provide a large surface area for contact with the hydrogen. Suitable packings include random packings, structured packings, grids or balls.

According to a second aspect of the present invention there is provided a process for the purification of an aromatic carboxylic acid, the process comprising:

introducing a liquid stream of crude aromatic carboxylic acid and hydrogen into the reaction vessel of the above mentioned first aspect, operating under hydrogenation conditions; and recovering a purified aromatic carboxylic acid from the reaction vessel.

The invention is particularly suitable to the production of purified terephthalic acid or purified isophthalic acid.

The reaction vessel and process will be operated such that the hydrogenation catalyst bed is fully flooded by the hydrogen saturated solution of aromatic carboxylic acid. Any suitable heterogeneous hydrogenation catalyst may be used. Suitable catalysts include those comprising Group VIII noble metals. The catalyst used may be supported or unsupported. Where a support is used it will be selected such that it is not dissolved in the reaction conditions. Suitable supports include carbon and charcoal as these are inert. Examples of suitable commercially available catalysts include D3065 supplied by Chimet, catalysts available from BASF, and H2Max50 or H2Max HD available from Sud-Chemie.

The hydrogenation reaction conditions required will depend on the carboxylic acid being treated and the solvent used. Typical reaction conditions for the purification of terephthalic acid are a temperature of about 270° C. to about 290° C. and a pressure of about 60 barg to about 90 barg. Typical reaction conditions for the purification of isophthalic acid are a temperature of about 200° C. to about 240° C. and a pressure of about 20 barg to about 40 barg.

The invention will now be described by way of example, with reference to the formation of terephthalic acid and with particular reference to the accompanying drawings in which:

FIG. 1 illustrates one embodiment of the reactor vessel of the present invention.

It will be understood that many other items of equipment which are not present in the drawings may be required. Such additional items include, but are not limited to, pumps, holding tanks, valves, pressure sensors, temperature sensors, pressure controllers, temperature controllers, level sensors, heaters, coolers, surge tanks, condensers, column reboilers and the like. Any such item of equipment would be installed in accordance with conventional engineering practice.

As illustrated in FIG. 1 the reactor comprises a reactor vessel 1. A bed of hydrogenation catalyst 2 is located at the bottom of the reactor vessel 1. Hydrogen is added through an inlet 3. Additionally or alternatively, hydrogen may be added below the packed bed.

A liquid holdup section 4 is provided around a downcomer 5. The solution of crude aromatic carboxylic acid is introduced into the reaction vessel 1 in line 6. A slurry of the crude aromatic carboxylic acid may also be used and dissolution will be completed in the liquid holdup section 4. The central downcomer 5 is packed to form the packed bed. The arrows illustrate the liquid flow path. Liquid from the liquid holdup section 4 will overflow into the downcomer packed bed 5.

Hydrogenation of the impurities occurs when the hydrogen saturated liquid contacts the hydrogenation catalyst bed 2. The stream comprising the hydrogenated impurities and the aromatic carboxylic acid is then removed in outlet 8.

The distance between the liquid level 7 and the bottom of the liquid holdup/packed sections 9, 10 can be minimised and be set according to good engineering practice which is sufficient to measure and control the liquid level above the hydrogenation catalyst bed rather than be dictated by the need to provide liquid height for hydrogen mass transfer.

The invention claimed is:

1. A reaction vessel for the purification of crude aromatic carboxylic acid comprising:
   a bed of hydrogenation catalyst having a vapor space located above said hydrogenation catalyst bed;
   a packed bed and a holdup section located within the vapor space and spaced above said catalyst bed;
   means for introducing a liquid comprising crude aromatic carboxylic acid and means for introducing hydrogen gas to the reaction vessel at respective locations such that in use the liquid comprising crude carboxylic acid contacts the hydrogen gas in the packed bed; and
   means for removing purified aromatic carboxylic acid.

2. The reaction vessel according to claim 1 wherein the means for introducing the hydrogen gas is located at or near the top of the vessel.

3. The reaction vessel according to claim 1 wherein means for introducing hydrogen gas is configured to introduce the hydrogen below the packed bed or into the liquid holdup section.

4. The reaction vessel according to claim 1 wherein a plurality of packed beds is provided spaced one from another.

5. The reaction vessel according to claim 1 wherein the liquid holdup section is located above the packed bed.

6. The reaction vessel according to claim 5 wherein the packed bed extends across the reactor.

7. The reaction vessel according to claim 1 wherein the liquid holdup section is located as one of an annulus around a central downcomer and a central region within an annular downcomer.

8. The reaction vessel according to claim 7 wherein the inlet means for the aromatic carboxylic acid is located one of at-and near the bottom of the liquid holdup section.

9. The reaction vessel according to claim 7 wherein the packed bed is located one of below the downcomer and within the downcomer.

10. The reaction vessel according to claim 1 wherein packing in the packed bed comprises at least one of: random packings, structured packings, grids and balls.

11. A process for the purification of an aromatic carboxylic acid, the process comprising:
    introducing a liquid stream of crude aromatic carboxylic acid and hydrogen into the reaction vessel according to claim 1 operating under hydrogenation conditions; and
    recovering a purified aromatic carboxylic acid from the reaction vessel.

12. The process according to claim 11 wherein the aromatic carboxylic acid is terephthalic acid.

13. The process according to claim 12 wherein hydrogenation is carried out at a temperature of about 270° C. to about 290° C. and a pressure of about 60 barg to about 90 barg.

14. The process according to claim 11 wherein the aromatic carboxylic acid is isophthalic acid.

15. The process according to claim 14 wherein hydrogenation is carried out at a temperature of about 200° C. to about 240° C. and a pressure of about 20 barg to about 40 barg.

* * * * *